US010045542B2

(12) United States Patent
Pullen

(10) Patent No.: US 10,045,542 B2
(45) Date of Patent: Aug. 14, 2018

(54) CITRUS OIL COMPOSITIONS AND METHODS OF USE

(75) Inventor: Erroll M. Pullen, Dennegeur (ZA)

(73) Assignee: Oro Agri, Inc., Trophy Club, TX (US)

( * ) Notice: Subject to any disclaimer, the term of this patent is extended or adjusted under 35 U.S.C. 154(b) by 1106 days.

(21) Appl. No.: 12/449,358

(22) PCT Filed: Feb. 6, 2008

(86) PCT No.: PCT/US2008/001530
§ 371 (c)(1),
(2), (4) Date: Oct. 14, 2010

(87) PCT Pub. No.: WO2008/097553
PCT Pub. Date: Aug. 14, 2008

(65) Prior Publication Data
US 2011/0281725 A1 Nov. 17, 2011

Related U.S. Application Data

(60) Provisional application No. 60/899,625, filed on Feb. 6, 2007.

(51) Int. Cl.
A01N 65/36 (2009.01)
A01N 25/30 (2006.01)

(52) U.S. Cl.
CPC ............ A01N 65/36 (2013.01); A01N 25/30 (2013.01)

(58) Field of Classification Search
CPC .............................. A01N 65/36; A01N 25/30
USPC ........................................................ 504/206
See application file for complete search history.

(56) References Cited

U.S. PATENT DOCUMENTS

| | | |
|---|---|---|
| 3,584,119 A | 6/1971 | Langley |
| 4,039,588 A | 8/1977 | Wilson et al. |
| 4,049,828 A | 9/1977 | Cole |
| 4,379,168 A | 4/1983 | Dotolo |
| 4,610,881 A | 9/1986 | Bechgaard |
| 4,978,686 A | 12/1990 | Sotome |
| 5,087,353 A | 2/1992 | Todd et al. |
| 5,110,804 A | 5/1992 | Lee |
| 5,118,506 A | 6/1992 | Eichofer |
| 5,143,939 A | 9/1992 | Browning |
| 5,330,671 A | 7/1994 | Pullen et al. |
| 5,374,600 A | 12/1994 | Hozumi et al. |
| 5,389,257 A | 2/1995 | Todd et al. |
| 5,444,078 A | 8/1995 | Yu et al. |
| 5,527,482 A | 6/1996 | Pullen et al. |
| 5,641,847 A | 6/1997 | Hozumi et al. |
| 5,679,351 A | 10/1997 | Walter et al. |
| 5,693,344 A | 12/1997 | Knight et al. |
| 5,744,137 A | 4/1998 | Stone |
| 5,753,593 A | 5/1998 | Pullen et al. |
| 5,863,456 A | 1/1999 | Pullen |
| 5,871,765 A | 2/1999 | Johnson et al. |
| 5,876,622 A | 3/1999 | Pullen et al. |
| 5,885,600 A | 3/1999 | Blum et al. |
| 5,900,243 A | 5/1999 | Yoder et al. |
| 5,948,743 A | 9/1999 | Fonsny et al. |
| 5,958,287 A | 9/1999 | Pullen |
| 5,977,186 A | 11/1999 | Franklin |
| 6,093,856 A | 7/2000 | Cripe et al. |
| 6,124,366 A | 9/2000 | Pullen et al. |
| 6,130,253 A | 10/2000 | Franklin et al. |
| 6,248,710 B1 | 6/2001 | Bijsterbosch et al. |
| 6,251,951 B1 | 6/2001 | Emerson et al. |
| 6,258,369 B1 | 7/2001 | Pullen |
| 6,277,389 B1 | 8/2001 | Pullen |
| 6,455,086 B1 | 9/2002 | Trinh et al. |
| 6,500,445 B1 | 12/2002 | Pullen |
| 6,514,512 B1 | 2/2003 | Puterka et al. |
| 6,582,712 B2 | 6/2003 | Pullen |
| 6,689,342 B1 | 2/2004 | Pan et al. |
| 7,294,341 B2 | 11/2007 | Pullen |
| 7,341,735 B2 | 3/2008 | Pullen |
| 8,092,817 B2 | 1/2012 | Pullen et al. |
| 2003/0035852 A1 | 2/2003 | Pullen |
| 2003/0060379 A1 | 3/2003 | Souter et al. |
| 2003/0224939 A1 | 12/2003 | Miles |
| 2004/0138176 A1 | 7/2004 | Miles |
| 2004/0242428 A1 | 12/2004 | Pullen |
| 2008/0064603 A1 | 3/2008 | Pullen |
| 2008/0070787 A1 | 3/2008 | Pullen |
| 2008/0166437 A1 | 7/2008 | Rosskopf et al. |

(Continued)

FOREIGN PATENT DOCUMENTS

| | | |
|---|---|---|
| EP | 0943239 A1 | 5/2009 |
| WO | 1996039846 | 12/1996 |

(Continued)

OTHER PUBLICATIONS

International Search Report and Written Opinion dated Aug. 8, 2008 for PCT/US2008/001530.
Tripathi, N. N. et al., "Toxicity of Some Terpenoids Against Fungi Infesting Fruits and Seeds of *Capsicum-Annuum* L. During Storage", Phytopatologische Zeitschrift, Verlag Paul Parey, Berlin, DE vol. 110, 1984, pp. 328-335.
Chery Lin, Chemical Constituents of Essential Oils, May 2007.
Bauske, et al., "Management of Meloidogyne Incognita on Cotton by Use of Botanical Compounds", Nematropica 24:142-150 (1994).

*Primary Examiner* — John Pak
*Assistant Examiner* — Andriae M Holt
(74) *Attorney, Agent, or Firm* — Knobbe Martens Olson & Bear, LLP

(57) ABSTRACT

Novel, environmentally safe compositions for the control of pests and methods of using these compositions are disclosed. The compositions may comprise one or more high terpene (50% by weight or more) based oils, such as but not limited to citrus oil, surfactants and other ingredients disclosed herein. Preferably, the one or more high terpene (50% by weight or more) based oils, such as but not limited to citrus oil, is cold pressed orange oil.

26 Claims, No Drawings

(56) References Cited

U.S. PATENT DOCUMENTS

2008/0214400 A1 9/2008 Pullen
2010/0144534 A1 6/2010 Pullen

FOREIGN PATENT DOCUMENTS

| WO | 1997016975 | 5/1997 |
|---|---|---|
| WO | WO1998/02044 A1 | 1/1998 |
| WO | 2000049865 A2 | 8/2000 |
| WO | 2001013726 | 3/2001 |
| WO | 2001026457 A2 | 4/2001 |
| WO | WO2003/020024 A2 | 3/2003 |
| WO | 2003056917 A2 | 7/2003 |
| WO | 2005070213 A2 | 8/2005 |
| WO | 2006/052228 A1 | 5/2006 |
| WO | 2008/097553 | 8/2008 |
| WO | 2011031287 | 3/2011 |

CITRUS OIL COMPOSITIONS AND METHODS OF USE

The instant application claims priority to U.S. Provisional Patent Application 60/899,625 filed Feb. 6, 2007, the disclosure of which is hereby incorporated by reference in its entirety.

FIELD OF THE INVENTION

The present invention relates to novel, environmentally safe compositions comprising one or more surfactants, one or more high terpene (50% by weight or more) based oils, one or more stabilizers, one or more chelating agents, one or more preservatives, one or more acidic pH adjusters and one or more organic solvents.

The invention is also directed to methods of using the disclosed compositions in environmentally safe procedures for the control of pests on transgenic or non-transgenic plants. All publications, patents and references cited herein are hereby incorporated by reference in their entireties.

BACKGROUND

Environmentally safe methods for the control of plant pests using non-toxic agents represent ecologically sound alternatives to the use of synthetic chemical pesticides, insecticides, fungicides, miticides, adjuvants for crop-care chemicals and the like. Damage caused to the environment, including natural aquifers and animal and plant species due to runoff of these chemicals is an ecological problem faced by virtually every country in the world. This environmental damage leads to enormous difficulties reflected in, for example, increased health care costs and ecological harm. There is a significant unmet need for environmentally safe methods for the control of pests using agents having low phytotoxicity but which have high activity against target pests.

The present inventors have discovered and disclose herein novel compositions for use in environmentally safe methods for the control of pests and/or "boosting" by the composition when used as an adjuvant.

SUMMARY OF THE INVENTION

The present invention is directed in part to compositions comprising one or more surfactants, one or more high terpene (50% by weight or more) based oils, one or more stabilizers, one or more chelating agents, one or more preservatives, one or more acidic pH adjusters and one or more organic solvents. In certain embodiments, said compositions may be used as stand-alone insecticides, miticides, fungicides, or nematicides. In other embodiments, the disclosed compositions may be used as adjuvants to boost the activity or efficacy of other agents such as insecticides, miticides, fungicides, nematicides, herbicides, fertilizers, nutrients and plant growth regulators.

In certain embodiments, the compositions of the invention comprise one or more surfactants which may be comprised of alcohol ethoxylate and alcohol ethoxy sulfate. In further embodiments, said compositions comprise about 10.0% by weight to about 15.0% by weight alcohol ethoxylate and about 4.0% by weight to about 8.0% by weight alcohol ethoxy sulfate. In still further embodiments, the compositions comprise about 12.0% by weight to about 14% by weight alcohol ethoxylate and about 5.0% by weight to about 7.0% by weight alcohol ethoxy sulfate. In still further embodiments, the compositions comprise about 13.5% by weight alcohol ethoxylate and about 6.0% by weight alcohol ethoxy sulfate.

In certain embodiments, the compositions of the invention comprise a high terpene based oil which is a citrus oil. In further embodiments said citrus oil is selected from the group consisting of orange oil, lemon oil, lime oil, grapefruit oil and tangerine oil. In a preferred embodiment, said orange oil is cold pressed orange oil. In a further preferred embodiment, said composition comprises about 3.0% by weight to about 7.0% by weight cold pressed orange oil. In a further preferred embodiment, said composition comprises about 4.0% by weight to about 6.0% by weight cold pressed orange oil. In a still further preferred embodiment, said composition comprises about 5.5% by weight cold pressed orange oil.

In certain embodiments, the compositions of the invention comprise one or more stabilizers which may be comprised of polyethylene glycol and urea. In a preferred embodiment, said compositions comprises about 0.2% by weight to about 0.5% by weight polyethylene glycol and about 0.2% by weight to about 0.5% by weight urea. In a further preferred embodiment, said compositions comprises about 0.4% by weight polyethylene glycol and about 0.4% by weight urea.

In certain embodiments, the compositions of the invention comprise one or more chelating agents which are comprised of ethylenediaminetetraacetic acid (EDTA). In a preferred embodiment, said compositions comprises about 0.2% by weight to about 0.5% by weight EDTA. In a further preferred embodiment, said compositions comprises about 0.4% by weight EDTA.

In certain embodiments, the compositions of the invention comprise one or more preservatives which may be comprised of propyl paraben and methyl paraben. In further embodiments, said compositions comprises about 0.05% by weight to about 0.5% by weight propyl paraben and about 0.05% by weight to about 0.5% by weight methyl paraben. In still further embodiments, said compositions comprise about 0.10% by weight propyl paraben and about 0.10% by weight methyl paraben.

In certain embodiments, the compositions of the invention comprise one or more acidic pH adjusters which may be comprised of citric acid.

In certain embodiments, the organic solvents of the compositions of the invention may be comprised of ethanol. In a preferred embodiment, said compositions comprise about 1.0% to about 7.0% by weight ethanol. In a still further embodiment, said compositions comprise about 5.5% by weight ethanol.

In certain preferred embodiments, the adjuvant compositions of the invention comprise alcohol ethoxylate, alcohol ethoxy sulfate, cold pressed orange oil, polyethylene glycol, urea, EDTA, propyl paraben, methyl paraben, citric acid and ethanol, wherein the components of said adjuvant composition are present in amounts effective to function as an adjuvant for fungicides, miticides, insecticides, nutrients, herbicides or plant growth regulators.

In still further embodiments of the invention, the adjuvant compositions comprise about 13.5% by weight alcohol ethoxylate, about 6.0% by weight alcohol ethoxy sulfate, about 5.5% by weight cold pressed orange oil, about 0.4% by weight polyethylene glycol, about 0.5% by weight urea, about 0.4% by weight EDTA, about 0.1% by weight propyl paraben and about 0.1% by weight methyl paraben.

The invention disclosed herein is also directed to methods of controlling pests on transgenic or non-transgenic plants comprising application of the compositions disclosed herein to a transgenic or non-transgenic plant to thereby control said pests.

The methods of application disclosed herein may be selected from the group consisting of spraying, wetting, dipping, misting, drenching, showering, fogging, soaking, dampening, drizzling, dousing and splashing.

In a preferred embodiment, the invention is directed to a method of applying an adjuvant composition to a target plant comprising, diluting the oil-containing compositions described herein into an aqueous composition comprising one or more agents selected from the group consisting of insecticides, miticides, fungicides, herbicides, nutrients, fertilizers, and plant growth regulators, wherein said oil-containing composition is diluted at a rate of about 1 part oil-containing composition to about 2000-2500 parts said aqueous composition. In certain preferred embodiments, said oil-containing composition is diluted at a rate of about 1 part oil-containing composition to about 2000 parts aqueous composition.

In certain embodiments, the compositions of the invention may be mixed or stored with one or more active agents including but not limited to insecticides, miticides, fungicides, herbicides, fertilizers, nutrients, fertilizers or plant growth regulators. In certain embodiments, the active agents include but are not limited to abamectin, Imidacloprid, chlorothalinol, permethryn, glufosinate and glyphosate.

DETAILED DESCRIPTION

As used herein, the terms "terpene" or "high terpene" refer to any of a class of chemical compounds that are widespread in nature, mainly in plants as constituents of essential oils. Many terpenes are hydrocarbons, but oxygen-containing compounds such as alcohols, aldehydes or ketones (terpenoids) are also found. Their building block is the hydrocarbon isoprene, $CH_2=C(CH_3)-CH=CH_2$. Certain terpene hydrocarbons have molecular formulas $(C_5H_8)_n$, and may be classified according to the number of isoprene units. When terpenes are modified chemically, such as by oxidation or rearrangement of the carbon skeleton, the resulting compounds are generally referred to as "terpenoids." As used herein, the term "terpene" includes all "terpenoids." Examples of monoterpenes are: pinene, nerol, citral, camphor, menthol, limonene. Examples of sesquiterpenes are: nerolidol, farnesol. Examples of diterpenes are: phytol, vitamin $A_1$. Squalene is an example of a triterpene, and carotene (provitamin $A_1$) is a tetraterpene.

As used herein, the terms "pesticidal effect" and "pesticidal activity" mean any direct or indirect action on the target pest that results in reduced feeding damage on any part of the plant, including but not limited to the seeds, roots, shoots and foliage of plants as compared to untreated plants.

The terms "active against a (first or second) pest", also have the same meaning. Such direct or indirect effects include inducing death of the pest, repelling the pest from any part of the plant, including but not limited to seeds, roots, shoots and/or foliage, inhibiting feeding of the pest on, or the laying of its eggs on, the plant seeds, roots, shoots and/or foliage, and inhibiting or preventing reproduction of the pest.

"Plant pest" means any organism known to associate with plants and which, as a result of that association, causes a detrimental effect on the plant's health and vigor. Plant pests include but are not limited to fungi, bacteria, viruses, molds, insects, mites and nematodes or any other organism that causes a detrimental effect on the plant's health or vigor, excluding mammals, fish and birds.

The term "plant" as used herein encompasses whole plants and parts of plants such as roots, shoots, stems, leaves, seedlings, germinated seeds and seed, as well as cells and tissues within the plants or plant parts.

The term "insecticidal activity" has the same meaning as pesticidal activity, except it is limited to those instances where the pest is an insect.

As used herein, the "shoots and foliage" of a plant are to be understood to be the shoots, stems, branches, leaves and other appendages of the stems and branches of the plant after the seed has sprouted, including the roots of the plant. It is preferable that the shoots and foliage of a plant be understood to be those parts of the plant that have grown from the seed and/or shoots of a "mother" plant.

As used herein, the "region of the seed" is to be understood to be that region within about one inch of the seed.

The one or more high terpene (50% by weight or more) based oils, such as, but not limited to, citrus oil compositions of the present invention can be in the form of a liquid or solid solution; suspension; emulsion; emulsion concentrate; slurry of particles in an aqueous medium (e.g., water); wettable powder; wettable granules (dry flowable); dry granules; stake, or stick. The concentration of the active ingredients in the formulation is preferably about 0.5% to about 99% by weight (w/w), preferably 5-40%.

Preferably, the one or more high terpene (50% by weight or more) based oils such as but not limited to citrus oil compositions of the invention may comprise from about 0.5% to about 99%, or preferably about 1% to about 30% one or more high terpene (50% by weight or more) based oils such as but not limited to citrus oil by weight. In certain preferred embodiments, the one or more high terpene (50% by weight or more) based oils such as but not limited to citrus oil compositions of the invention may comprise about 5% to about 20%, or about 12% to about 20% or about 12% to about 18% or about 12.7% citrus oil by weight.

Preferably, the one or more high terpene (50% by weight or more) based oils such as but not limited to citrus oil compositions of the invention may comprise about 3% to about 90% by weight surfactant or any percent by weight within this range. Preferably, about 5% to about 20% by weight surfactant. When used as an adjuvant, the final surfactant concentration is preferably about 0.25% to about 0.8% by weight surfactant. In some embodiments, this may be from about 0.25% to about 0.33% by weight surfactant. In other embodiments, the surfactant is present at about 0.05% by weight to about 0.2% by weight and in other embodiments between about 0.025% to about 0.05%.

In certain embodiments, the one or more high terpene (50% by weight or more) based oils such as but not limited to citrus oil compositions of the invention may further comprise one or more insecticides, fungicides, miticides, herbicides, nutrients, plant growth regulators and/or fertilizers. In these embodiments, the one or more high terpene (50% by weight or more) based oils such as but not limited to citrus oil compositions of the invention may comprise about 0.5% to about 65% insecticides, fungicides, miticides, herbicides, nutrients, plant growth regulators and/or fertilizers by weight. In certain preferred embodiments, the one or more high terpene (50% by weight or more) based oils such as but not limited to citrus oil compositions of the invention may comprise about 90% to about 99.99% insecticides, fungicides, miticides, herbicides, nutrients, plant growth regulators and/or fertilizers by weight.

In certain embodiments of the one or more high terpene (50% by weight or more) based oils such as but not limited to citrus oil compositions contemplated herein, the pH of the composition is between about 6.0 to about 9.0 or preferably about 7.8 to about 8.0.

In certain embodiments, the one or more high terpene (50% by weight or more) based oils such as but not limited to citrus oil compositions of the invention may be diluted with water prior to use. Preferably, the citrus oil compositions may be diluted by combining from about 1 part one or more high terpene (50% by weight or more) based oils such as but not limited to citrus oil composition with about 2,000 parts water (1:2000); or about 2.5 parts citrus oil composition with about 100 parts water (2.5:100). In certain embodiments, when used with insecticides or fungicides, the compositions of the invention may be diluted with water by combining about 100 parts water with about 1 part of the composition (100:1) or any intervening dilution up to about 2000 parts water with about 1 part of the composition. When used as an adjuvant, the compositions of the invention may be combined with about 500 parts water with about 1 part composition or any intervening dilution up to about 2000 parts water or about 4000 parts water with about 1 part composition.

Other conventional inactive or inert ingredients can be incorporated into the citrus oil formulations. Such inert ingredients include but are not limited to: conventional sticking agents, dispersing agents such as methylcellulose (Methocel A15LV or Methocel A15C, for example, serve as combined dispersant/sticking agents for use in seed treatments), polyvinyl alcohol (e.g., Elvanol 51-05), lecithin (e.g., Yelkinol P), polymeric dispersants (e.g., polyvinylpyrrolidone/vinyl acetate PVP/VA S-630), thickeners (e.g., clay thickeners such as Van Gel B to improve viscosity and reduce settling of particle suspensions), emulsion stabilizers, surfactants, antifreeze compounds (e.g., urea), dyes, colorants, and the like.

Further inert ingredients useful in the present invention can be found in McCutcheon's, vol. 1, "Emulsifiers and Detergents," MC Publishing Company, Glen Rock, N.J., U.S.A., 1996. Additional inert ingredients useful in the present invention can be found in McCutcheon's, vol. 2, "Functional Materials," MC Publishing Company, Glen Rock, N.J., U.S.A., 1996.

Surfactants

The following compounds are provided as non-limiting examples of the surfactants:

Nonionic surfactants include agents such as sorbitan monolaurate, sorbitan monopalmitate, sorbitan sesquioleate, sorbitan trioleate, polyoxyethylene sorbitan monolaurate, polyoxyethylene sorbitan monostearate, polyethylene glycol monooleate, polyethylene glycol alkylate, polyoxyethylene alkyl ether, polyglycol diether, lauroyl diethanolamide, fatty acid iso-propanolamide, maltitol hydroxy fatty acid ether, alkylated polysaccharide, alkyl glucoside, sugar ester, oleophillic glycerol monostearate, self-emulsifiable glycerol monostearate, polyglycerol monostearate, polyglycerol alkylate, sorbitan monooleate, polyethylene glycol monostearate, polyoxyethylene sorbitan monooleate, polyoxyethylene cetyl ether, polyoxyethylene sterol, polyoxyethylene lanolin, polyoxyethylene bees wax, and polyoxyethylene hydrogenated castor oil; and the like.

Anionic surfactants include agents such as sodium stearate, potassium palmitate, sodium cetyl sulfate, sodium lauryl phosphate, sodium polyoxyethylene lauryl sulfate, triethanolamine palmitate, polyoxyethylene sodium lauryl phosphate, and sodium N-acyl glutamate; and the like.

Cationic surfactants include agents such as stearyl dimethylbenzyl ammonium chloride, stearyl trimethyl ammonium chloride, benzalkonium chloride, and laurylamine oxide; and the like.

Amphoteric surfactants such as alkylaminoethyl glycine chloride and lecithin; and the like.

Calfoam® ES-603 is a clear liquid sodium salt of alcohol ethoxy sulfate with a faint alcohol odor. This biodegradable surfactant is pourable and pumpable at ambient temperatures and functions as a flash foamer and foam stabilizer in aqueous systems.

TERGITOL™ 15-S-9 Surfactant is known chemically as secondary alcohol ethoxylate. It is a non-ionic surfactant.

Citrus Oils and One or More High Terpene (50% by Weight or more) Based Oils

Citrus oils include orange oil, lemon oil, lime oil, grapefruit oil and tangerine oil.

The one or more high terpene (50% by weight or more) based oils, such as but not limited to citrus oils, of the compositions and methods of the invention may be obtained by any method from the citrus fruit in question. In particular, citrus oils are obtained from the skin or peel of the fruit in question. Preferred methods of obtaining the citrus oil include but are not limited to cold pressing techniques. Examples of terpene containing oils that may be used in the compositions of the invention include, but are not limited to, pine oils and naturally occurring oils of plants that contain 50% or more terpenes.

Insecticides, Miticides and Fungicides

The terms "insecticide", "miticide", "fungicide" and "adjuvant for other crop protection chemicals", include any agent used primarily for the control of insects and/or mites or fungi by preventing, destroying, repelling or mitigating any insects and/or mites or fungi which may be present in any environment whatsoever. These terms include the concepts of "acaricide" (agent used primarily in the control of plant-feeding mites, especially spider mites), "nematicide" (agent used primarily for the control of root-infesting nematodes on crop plants), "insect pheromone" (agent used primarily for the control of behavioral responses of insects).

Herbicides

The citrus oil compositions of the invention may also comprise one or more herbicides.

Fertilizers and Nutrients

The invention compositions may also comprise fertilizers and nutrients (e.g. nitrogen-, potassium- or phosphorus-containing fertilizers). Compositions comprising only granules of fertilizer incorporating, for example coated with, the citrus oil compositions are preferred. Such granules suitably contain up to 25% by weight of the citrus oil composition. The invention therefore also provides a fertilizer composition comprising a fertilizer and the citrus oil compositions disclosed herein.

Plant Growth Regulators

Plant growth regulators, also known as plant hormones and phytohormones are chemicals that regulate plant growth. According to a standard animal definition, hormones are signal molecules produced at specific locations, that occur in very low concentrations, and cause altered processes in targeted cells at other locations. Plant hormones, on the other hand, are distinct from animal hormones, since they are often not transported to other parts of the plant and production in not limited to specific locations. Plants lack tissues or organs specifically for the production of hormones; unlike animals, plants lack glands that produce and secrete hormones that are then circulated around the body. Plant hormones shape the plant, affecting seed growth, time of flowering, the sex of flowers, senescence of leaves and fruits, they affect which tissues grow upward and which grow downward, leaf formation and stem growth, fruit development and ripening, plant longevity and plant death.

Plant Varieties and Crops

The citrus oil compositions disclosed herein are preferably used for agricultural and horticultural purposes in the form of a composition. The type of composition used in any instance will depend upon the particular purpose envisaged.

It is contemplated that the present methods can be used to protect the seeds, roots and/or the above-ground parts of field, forage, plantation, glasshouse, orchard or vineyard crops, grasses, turf, ornamentals, plantation, household or forest trees.

The plants that may be treated using the methods and compositions disclosed herein can be any species of plant. However, they are preferably the plant species that are agronomically or horticulturally important. In particular, the plant species can be corn, peanut, canola/rapeseed, soybean, curcubits, crucifers, cotton, beets, rice, sorghum, sugar beet, wheat, barley, rye, sunflower, tomato, sugarcane, tobacco, oats, as well as other vegetable and leaf crops. In certain embodiments, the crops or plant species may include vineyards, citrus, pecans, almonds, all stone fruits, apples, pears, bananas, lawns, turf, home & garden and garden varieties of plants.

The plants may also be any ornamental plants, including but not limited to rose, tulip, violet, daffodil, gladiolus, lavender, lilies, narcissus, orchid, hyacinth, chrysanthemum, crocus, iris, peonies, zephyranthes, carnation, anthurium, gloxinia, azalea, poinsettia, ageratum, bamboo, begonia, camellia, dahlia, dianthus, geranium, impatiens, lilies of the valley and lobelia.

In one embodiment of the invention, the plant or seed is a non-transgenic plant or seed.

In another embodiment of the invention, the plant or seed is a transgenic plant or seed from which a transgenic plant can grow. The transgenic plants and seeds of the present invention are engineered to express a desirable characteristic and, in particular, to have at least one heterologous gene encoding for the expression of a protein that is pesticidally active and, in particular, has insecticidal activity. The heterologous gene in the transgenic plant or seed of the present invention can be derived from a microorganism such as *Bacillus, Rhizobium, Pseudomonas, Serratia, Trichoderma, Clavibacter, Glomus, Gliocladium* and mycorrhizal fungi. In particular, it is contemplated that the present methods are especially beneficial when the heterologous gene is one that is derived from a *Bacillus* sp. microorganism and the protein is active against corn rootworm.

It is also contemplated that the present methods are especially beneficial when the heterologous gene is one that is derived from a *Bacillus* sp. microorganism and the protein is active against European corn borer. A preferred *Bacillus* sp. microorganism is *Bacillus thuringiensis*. It is particularly preferred when the heterologous gene encodes a modified Cry3Bb delta-endotoxin derived from *Bacillus thuringiensis*.

Methods of Application

The compositions disclosed herein can be applied in a number of ways. For example, they can be applied directly to the foliage of a plant, to seeds or to other media in which plants are growing or are to be planted, such as the furrow or in the immediate vicinity of the plant to the soil or where the seed is to be planted prior to sowing. Application methods include spraying, or dusting or applying as a cream or paste formulation, or applying as a vapor or as slow release granules.

The compositions may be applied using methods including but not limited to spraying, wetting, dipping, misting, drenching, showering, fogging, soaking, dampening, drizzling, dousing, aerial crop dusting via airplane or helicopter and splashing.

Application can be to any part of the plant or seed including the foliage, stems, branches or roots, or to soil surrounding the roots, or to the seed before it is planted, or to the soil generally, to paddy water or to hydroponic culture systems. The citrus oil compositions disclosed herein may also be injected into plants or sprayed onto vegetation using electrodynamic spraying techniques or other low volume methods.

The compositions may be in the form of dustable powders or granules comprising the citrus oil compositions in dry form and a solid diluent or carrier, for example, fillers such as kaolin, bentonite, kieselguhr, dolomite, calcium carbonate, talc, powdered magnesia, fuller's earth, gypsum, diatomaceous earth and china clay. Such granules can be preformed granules suitable for application to the soil without further treatment. These granules can be made either by impregnating pellets of filler with the citrus oil compositions or by pelleting a mixture of the citrus oil composition and powdered filler.

Compositions for dressing seed may include an agent (for example, a mineral oil) for assisting the adhesion of the citrus oil composition to the seed; alternatively the active ingredient can be formulated for seed dressing purposes using an organic solvent (for example, N-methylpyrrolidone, propylene glycol or N,N-dimethylformamide). The compositions may also be in the form of wettable powders or water dispersible granules comprising wetting or dispersing agents to facilitate the dispersion in liquids. The powders and granules may also contain fillers and suspending agents.

Emulsifiable concentrates or emulsions may be prepared by dissolving the citrus oil composition in an organic solvent optionally containing a wetting or emulsifying agent and then adding the mixture to water which may also contain a wetting or emulsifying agent. Suitable organic solvents are aromatic solvents such as alkylbenzenes and alkylnaphthalenes, ketones such as cyclohexanone and methylcyclohexanone, chlorinated hydrocarbons such as chlorobenzene and trichlorethane, and alcohols such as benzyl alcohol, furfuryl alcohol, butanol and glycol ethers.

Suspension concentrates of largely insoluble solids may be prepared by ball or bead milling with a dispersing agent with a suspending agent included to stop the solid settling.

Compositions to be used as sprays may be in the form of aerosols wherein the formulation is held in a container under pressure of a propellant, e.g. fluorotrichloromethane or dichlorodifluoromethane.

The citrus oil compositions can be mixed in the dry state with a pyrotechnic mixture to form a composition suitable for generating in enclosed spaces a smoke containing the citrus oil compositions.

Alternatively, the citrus oil compositions may be used in micro-encapsulated form. They may also be formulated in biodegradable polymeric formulations to obtain a slow, controlled release of the citrus oil composition.

By including suitable additives, for example additives for improving the distribution, adhesive power and resistance to rain on treated surfaces, the citrus oil compositions can be better adapted for various utilities.

Wettable powders, emulsifiable concentrates and suspension concentrates will normally contain surfactants, e.g. a wetting agent, dispersing agent, emulsifying agent or suspending agent. These agents can be cationic, anionic or non-ionic agents.

Seed Coatings

The one or more high terpene (50% by weight or more) based oils such as but not limited to citrus oil compositions of the invention may be used as seed coatings. Useful seed coatings contain one or more binders and at least one of the subject citrus oil compositions. Binders that are useful in the present invention preferably comprise an adhesive polymer that may be natural or synthetic and is without phytotoxic effect on the seed to be coated. The binder may be selected from polyvinyl acetates; polyvinyl acetate copolymers; polyvinyl alcohols; polyvinyl alcohol copolymers; celluloses, including ethylcelluloses, methylcelluloses, hydroxymethylcelluloses, hydroxypropylcelluloses and carboxymethylcellulose; polyvinylpyrolidones; polysaccharides, including starch, modified starch, dextrins, maltodextrins, alginate and chitosans; fats; oils; proteins, including gelatin and zeins; gum arabics; shellacs; vinylidene chloride and vinylidene chloride copolymers; calcium lignosulfonates; acrylic copolymers; polyvinylacrylates; polyethylene oxide; polyacrylamide polymers and copolymers; polyhydroxyethyl acrylate, methylacrylamide monomers; and polychloroprene.

The amount of binder in the coatings of the invention can vary, but will be in the range of about 0.01 to about 25% of the weight of the seed, more preferably from about 0.05 to about 15%, and even more preferably from about 0.1% to about 10%.

The citrus oil formulations of the invention can optionally include a filler. The filler can be an absorbent or an inert filler, such as are known in the art, and may include woodflours, clays, activated carbon, sugars, diatomaceous earth, cereal flours, fine-grain inorganic solids, calcium carbonate, and the like. Clays and inorganic solids which may be used include calcium bentonite, kaolin, china clay, talc, perlite, mica, vermiculite, silicas, quartz powder, montmorillonite and mixtures thereof. Sugars which may be useful include dextrin and maltodextrin. Cereal flours include wheat flour, oat flour and barley flour.

The filler is selected so that it will provide a proper microclimate for the seed, for example the filler is used to increase the loading rate of the active ingredients and to adjust the control-release of the active ingredients. The filler can aid in the production or process of coating the seed. The amount of filler can vary, but generally the weight of the filler components will be in the range of about 0.05 to about 75% of the seed weight, more preferably about 0.1 to about 50%, and even more preferably about 0.5% to 15%.

The exact amount of the combination of the active ingredients that is included in the coating is determined by one of skill in the art and will vary depending upon the size of the seed to be coated. The active ingredients of the coating must not inhibit germination of the seed and should be efficacious in protecting the seed and/or the plant during that time in the target insect's life cycle in which it causes injury to the seed or plant. In general, the coating will be efficacious for approximately 0 to 120 days after sowing.

The coating is particularly effective in accommodating high active ingredient loads, as can be required to treat typically refractory pests, such as corn root worm, while at the same time preventing unacceptable phytotoxicity due to the increased active ingredient load.

Optionally, a plasticizer can be used in the coating formulation. Plasticizers are typically used to make the film that is formed by the coating layer more flexible, to improve adhesion and spreadability, and to improve the speed of processing. Improved film flexibility is important to minimize chipping, breakage or flaking during storage, handling or sowing processes. Many plasticizers may be used, however, useful plasticizers include polyethylene glycol, glycerol, butylbenzylphthalate, glycol benzoates and related compounds. The range of plasticizer in the coating layer will be in the range of from bout 0.1 to about 20% by weight.

Target Pests

The target pest for the present invention include but are not limited to adult or larvae of any insect or other pest that feeds on the seed, roots and/or shoots and foliage of the plant that is to be protected by the subject methods and compositions. Such pests include but are not limited to: from the order Lepidoptera, for example, *Acleris* spp., *Adoxophyes* spp., *Aegeria* spp., *Agrotis* spp., *Alabama argillaceae, Amylois* spp., *Anticarsia gemmatalis, Archips* spp, *Argyrotaenia* spp., *Autographa* spp., *Busseola fusca, Cadra cautella, Carposina nipponensis, Chilo* spp., *Choristoneura* spp., *Clysia ambiguella, Cnaphalocrocis* spp., *Cnephasia* spp., *Cochylis* spp., *Coleophora* spp., *Crocidolomia binotalis, Cryptophlebia leucotreta, Cydia* spp., *Diatraea* spp., *Diparopsis castanea, Earias* spp., *Ephestia* spp., *Eucosma* spp., *Eupoecilia ambiguella, Euproctis* spp., *Euxoa* spp., *Grapholita* spp., *Hedya nubiferana, Heliothis* spp., *Hellula undalis, Hyphantria cunea, Keiferia lycopersicella, Leucoptera scitella, Lithocollethis* spp., *Lobesia botrana, Lymantria* spp., *Lyonetia* spp., *Malacosoma* spp., *Mamestra brassicae, Manduca sexta, Operophtera* spp., *Ostrinia Nubilalis, Pammene* spp., *Pandemis* spp., *Panolis flammea, Pectinophora gossypiella, Phthorimaea operculella, Pieris rapae, Pieris* spp., *Plutella xylostella, Prays* spp., *Scirpophaga* spp., *Sesamia* spp., *Sparganothis* spp., *Spodoptera* spp., *Synanthedon* spp., *Thaumetopoea* spp., *Tortrix* spp., *Trichoplusia ni* and *Yponomeuta* spp.; from the order Coleoptera, for example, *Agriotes* spp., *Anthonomus* spp., *Atomaria linearis, Chaetocnema tibialis, Cosmopolites* spp., *Curculio* spp., *Dermestes* spp., *Diabrotica* spp., *Epilachna* spp., *Eremnus* spp., *Leptinotarsa decemlineata, Lissorhoptrus* spp., *Melolontha* spp., *Orycaephilus* spp., *Otiorhynchus* spp., *Phlyctinus* spp., *Popillia* spp., *Psylliodes* spp., *Rhizopertha* spp., *Scarabeidae, Sitophilus* spp., *Sitotroga* spp., *Tenebrio* spp., *Tribolium* spp. and *Trogoderma* spp.; from the order Orthoptera, for example, *Blatta* spp., *Blattelia* spp., *Gryllotalpa* spp., *Leucophaea maderae, Locusta* spp., *Periplaneta* ssp., and *Schistocerca* spp.; from the order Isoptera, for example, *Reticulitemes* ssp; from the order Psocoptera, for example, *Liposcelis* spp.; from the order Anoplura, for example, *Haematopinus* spp., *Linognathus* spp., *Pediculus* spp., *Pemphigus* spp. and *Phylloxera* spp.; from the order Mallophaga, for example, *Damalinea* spp. and *Trichodectes* spp.; from the order Thysanoptera, for example, *Franklinella* spp., *Hercinothrips* spp., *Taeniothrips* spp., *Thrips palmi, Thrips tabaci* and *Scirtothrips auranti;* from the order Heteroptera, for example, *Cimex* spp., *Distantiella theobroma, Dysdercus* spp., *Euchistus* spp., *Eurygaster* spp., *Leptocorisa* spp., *Nezara* spp., *Piesma* spp., *Rhodnius* spp., *Sahlbergella singularis, Scotinophara* spp. and *Triatoma* spp.; from the order Homoptera, for example, *Aleurothrixus floccosus, Aleyrodes brassicae, Aonidiella* spp., *Aphididae, Aphis* spp., *Aspidiotus* spp., *Bemisia tabaci, Ceroplaster* spp., *Chrysomphalus aonidium, Chrysomphalus dictyospermi, Coccus hesperidum, Empoasca* spp., *Eriosoma larigerum, Erythroneura* spp., *Gascardia* spp., *Laodelphax* spp., *Lacanium comi, Lepidosaphes* spp., *Macrosiphus* spp., *Myzus* spp., *Nehotettix* spp., *Nilaparvata* spp., *Paratoria* spp., *Pemphigus* spp., *Planococcus* spp., *Pseudaulacaspis* spp., *Pseudococcus* spp., *Psylla* ssp., *Pulvinaria aethiopica, Quadraspidiotus* spp., *Rhopalosiphum* spp., *Saissetia* spp., *Scaphoideus* spp., *Schizaphis* spp., *Sitobion* spp., *Trialeurodes vaporariorum, Trioza erytreae* and *Unaspis citri*; from the order Hymenoptera, for example, *Acromyrmex, Atta* spp., *Cephus* spp., *Diprion* spp., *Diprionidae, Gilpinia polytoma, Hoplocampa* spp., *Lasius* sppp., *Monomorium pharaonis, Neodiprion* spp, *Solenopsis* spp. and *Vespa* ssp.; from the order Diptera, for example, *Aedes* spp., *Antherigona soccata, Bibio hortulanus, Calliphora erythrocephala, Ceratitis* spp., *Chrysomyia* spp., *Culex* spp., *Cuterebra* spp., *Dacus* spp., *Drosophila melanogaster, Fannia* spp., *Gastrophilus* spp., *Glossina* spp., *Hypoderma* spp., *Hyppobosca* spp., *Liriomysa* spp., *Lucilia* spp., *Melanagromyza* spp., *Musca* ssp., *Oestrus* spp., *Orseolia* spp., *Oscinella frit, Pegomyia hyoscyami, Phorbia* spp., *Rhagoletis pomonella, Sciara* spp., *Stomoxys* spp., *Tabanus* spp., *Tannia* spp. and *Tipula* spp., from the order Siphonaptera, for example, *Ceratophyllus* spp. and *Xenopsylla cheopis* and from the order Thysanura, for example, *Lepisma saccharina.*

EXAMPLES

Example 1

Orange Oil Composition ("OROBOOST")

An orange oil composition, referred to herein as "OROBOOST," is prepared by combining the following. OROBOOST may be used alone or in combination with an agriculturally effective active agent. When used in combination with an agriculturally effective active agent as an adjuvant, efficacy/response of translaminar and systemic type insecticides, miticides, fungicides, plant growth regulators, herbicides, nutrients, fertilizers and dormant oils increase using OROBOOST.

Example 2

Mixing OROBOOST with an Active Agent

Spray tank is filled on-half full with water. The required amount of active agent is added while agitating. The remainder of water is added to the tank. The recommended amount of OROBOOST is added last and agitated until the completion of spraying. The active agent may be any agriculturally effective active agent including, but not limited to, abamectin, Imidacloprid, chlorothalinol, permethryn, glufosinate or glyphosate.

Example 3

USE of OROBOOST as an Adjuvant in Season with Insecticides, Miticides, Fungicides, Herbicides, Nutrients and Plant Growth Regulators About 20 to about 100 fluid ounces OROBOOST is used per 100 gallons of tank-mix spray solution. The tank-mix may also contain any agriculturally effective active agent including, but not limited to, abamectin, Imidacloprid, chlorothalinol, permethryn, glufosinate or glyphosate.

Example 4

Use of OROBOOST Post Harvest, Dormant and Delayed Dormant with Insecticides, Miticides, Fungicides, Herbicides, Nutrients, Plant Growth Regulators and/or Dormant Oils One to three quarts of OROBOOST per acre to be sprayed are added in sufficient tank-mix spray water volume to adequately wet target.

| Ingredient | % By Weight | Supplier Name | Purpose in Formulation |
| --- | --- | --- | --- |
| Alcohols, C11-15-Secondary, ethoxylated, Tergitol 15-S-9 [068131-40-8] | 13.58 | DOW Chemical, UK | Surfactant |
| Polyethylene glycol, Tergitol 15-S-9 [25322-68-3] | 0.42 | DOW Chemical, UK | Stabilizer |
| SLES, Calfoam ES-603 [9004-82-4] | 6.00 | Pilot Chemical Co. | Scouring/coupling agent/Surfactant |
| Ethanol, Calfoam ES-603 [64-17-5] | 1.50 | Pilot Chemical Co. | SLES solvent |
| Ethanol, [64-17-5] | 4.00 | AAPER Alcohol & Chemical Co. | Co-solvent |
| Cold pressed orange oil, [8008-57-9] | 5.50 | Haarmann & Reimer | Fragrance/spreader |
| Urea, [57-13-6] | 0.46 | PCS Sales | Stabilizer |
| Ethylenediaminetetraacetic acid, terta sodium salt, Dissolvine 220-S [64-02-8] | 0.40 | AKZO Nobel | Chelating agent/pH buffer |
| Propyl Paraben, Propyl p-hydroxybenzoate, [99-13-3] | 0.10 | Acme-Hardesty | Preservative |
| Methyl Paraben, Methyl p-hydroxybenzoate, [99-76-3] | 0.10 | Acme-Hardesty | Preservative |
| Citric Acid, [77-92-9] | As Needed | Chemicals, Inc. | pH adjuster as needed |
| Water, [7732-18-5] | 67.94 | Tap Water | Diluent |
| Total | 100 | | |

Example 5

Use of OROBOOST as an Adjuvant with an Insecticide

One part up to about 80 parts OROBOOST is diluted into about 2000 parts water-containing insecticide formulation. The mixture is sprayed onto target plants using conventional agricultural spraying equipment.

The invention claimed is:

1. A composition, comprising:
   about 10% by weight to about 14% by weight $C_{11-15}$ alcohol ethoxylate;
   about 5.0% by weight to about 7.0% by weight alcohol ethoxy sulfate;
   about 3.0% by weight to about 7.0% by weight citrus oils;
   about 0.2% by weight to about 0.5% by weight polyethylene glycol;
   about 0.2% by weight to about 0.5% by weight urea;
   about 0.2% by weight to about 0.5% by weight chelating agent;
   one or more preservatives;
   one or more acidic pH adjusters; and
   about 1.0% to about 7.0% by weight of one or more organic solvents.

2. The composition of claim 1, wherein the chelating agent is EDTA.

3. The composition of claim 1, wherein said one or more preservatives are comprised of propyl paraben and methyl paraben.

4. The composition of claim 3, wherein said composition comprises about 0.05% by weight to about 0.5% by weight propyl paraben and about 0.05% by weight to about 0.5% by weight methyl paraben.

5. The composition of claim 4, wherein said composition comprises about 0.10% by weight propyl paraben and about 0.10% by weight methyl paraben.

6. The composition of claim 1, wherein said one or more acidic pH adjusters are comprised of citric acid.

7. The composition of claim 1, wherein said one or more organic solvents are comprised of ethanol.

8. The composition of claim 7, wherein said composition comprises about 1.0% to about 7.0% by weight ethanol.

9. The composition of claim 8, wherein said composition comprises about 5.5% by weight ethanol.

10. The composition of claim 1, wherein the citrus oils comprise cold pressed orange oil, wherein the one or more preservatives consist of about 0.05% by weight to about 0.5% by weight propyl paraben and from about 0.05% by weight to about 0.5% by weight methyl paraben, wherein the one or more acidic pH adjusters consist of citric acid, and wherein the one or more organic solvents consist of ethanol.

11. The composition of claim 10, further comprising one or more agents selected from the group consisting of abamectin, Imidacloprid, chlorthalimol, permethryn, glufosinate and glyphosate.

12. The composition of claim 1, wherein the one or more acidic pH adjusters is present in the composition in an amount such that a pH of the composition is adjusted to between about 6.0 and about 9.0.

13. The composition of claim 1, further comprising glyphosate.

14. The composition of claim 2, further comprising glyphosate.

15. An adjuvant composition comprising from about 10.0% by weight to about 15.0% by weight $C_{11-15}$ alcohol ethoxylate, from about 4.0% by weight to about 8.0% by weight alcohol ethoxy sulfate, from about 1% to about 30% by weight of citrus oil, from about 0.2% to 0.5% by weight one or more stabilizers comprising polyethylene glycol and urea, from about 0.2% to about 0.5% by weight of a chelating agent, one or more preservatives selected from the group consisting of propyl paraben and methyl paraben, one or more acidic pH adjusters comprising citric acid, and from about 1.0% to about 7.0% by weight of one or more organic solvents.

16. The adjuvant composition of claim 15, comprising about 13.5% by weight $C_{11-15}$ alcohol ethoxylate, about 6.0% by weight alcohol ethoxy sulfate, about 5.5% by weight cold pressed orange oil, about 0.4% by weight polyethylene glycol, about 0.5% by weight urea, about 0.4% by weight chelating agent, about 0.1% by weight propyl paraben and about 0.1% by weight methyl paraben, wherein the chelating agent is EDTA.

17. The composition of claim 1 or claim 15 further comprising one or more agents selected from the group consisting of fungicides, miticides, insecticides, nutrients, herbicides and plant growth regulators.

18. The composition of claim 17, wherein said agent is selected from the group consisting of abamectin, Imidacloprid, chlorothalimol, permethryn, glufosinate and glyphosate.

19. A method of controlling pests on transgenic or non-transgenic plants comprising application of the composition of claim 1 or 15 to a transgenic or non-transgenic plant to thereby control said pests.

20. The method of claim 19, wherein said plant is a non-transgenic plant.

21. The method of claim 19, wherein said plaint is a transgenic plant.

22. The method of claim 19, wherein said application is selected from the group consisting of spraying, wetting, dipping, misting, drenching, showering, fogging, soaking, dampening, drizzling, dousing and splashing.

23. The method of claim 22, wherein said application is spraying.

24. The method of claim 19, wherein said pest is an insect, mite, fungus, mold, bacteria, virus or nematode.

25. A method of applying a composition to a target plant comprising:
   diluting the composition of claim 1 or claim 15 into an aqueous composition comprising one or more agents selected from the group consisting of insecticides, miticides, fungicides, herbicides, nutrients and plant growth regulators, wherein said composition of claim 1 or claim 15 is diluted at a rate of about 1-part composition of claim 1 or claim 15 to about 2000-2500 parts said aqueous composition to yield a diluted composition; and
   applying the diluted composition to a target plant, whereby a plant pest is controlled.

26. The method of claim 25, wherein the composition of claim 1 or claim 15 is diluted at a rate of about 1-part composition of claim 1 or claim 15 to about 2000 parts aqueous composition.

* * * * *